United States Patent [19]

Dürr et al.

[11] Patent Number: 5,026,280

[45] Date of Patent: Jun. 25, 1991

[54] ENOSSAL IMPLANT WITH AN ELASTIC INTERMEDIATE ELEMENT AND A METAL SPACER ELEMENT

[75] Inventors: Walter Dürr, Remchingen; Axel Kirsch, Filderstadt, both of Fed. Rep. of Germany

[73] Assignee: IMZ Fertigungs und Vertriebsgellschaft fur dentale Technologie mbH, Fed. Rep. of Germany

[21] Appl. No.: 440,257

[22] Filed: Nov. 22, 1989

[30] Foreign Application Priority Data

Nov. 24, 1988 [DE] Fed. Rep. of Germany ....... 3839724
Mar. 23, 1989 [DE] Fed. Rep. of Germany ....... 3909580

[51] Int. Cl.$^5$ ................................................. A61C 8/00
[52] U.S. Cl. .................................... 433/175; 433/173; 433/177
[58] Field of Search ................ 433/173, 169, 174, 176, 433/177, 175, 201.1; 623/16, 66

[56] References Cited

U.S. PATENT DOCUMENTS

| 4,416,629 | 11/1983 | Mozsary et al. | 433/174 |
| 4,552,532 | 11/1985 | Mozsary | 433/174 X |
| 4,731,085 | 3/1988 | Koch | 623/16 |
| 4,756,689 | 7/1988 | Lundgren et al. | 433/173 |
| 4,758,160 | 7/1988 | Ismail | 433/173 |
| 4,780,080 | 10/1988 | Haris | 433/173 |
| 4,781,591 | 11/1988 | Allen | 433/173 X |
| 4,793,808 | 12/1988 | Kirsch | 433/173 |
| 4,938,693 | 7/1990 | Bulakiev | 433/169 |
| 4,950,161 | 8/1990 | Richter | 433/169 |

Primary Examiner—Alan W. Cannon
Attorney, Agent, or Firm—Hill, Van Santen, Steadman & Simpson

[57] ABSTRACT

An enossal or endosteal implant with a fastening head and fastening arrangment having a metal implant post screwable into a basic structure for snugly fitting a conditionally removable denture with a spacer element provided with a centering collar being inserted into the open end of the basic structure and engageable with a shoulder of an upper edge of the basic structure and an intermediate element having a portion made of an elastic material is characterized by the spacer element being made of metal and having a closed end remote from the fastening head for the denture and being threaded into the basic structure; the intermediate element is insertable in a socket formed by a counterbore at the open end of the spacer element and is provided with a ring shoulder for engaging an upper edge of the spacer element, and the intermediate element has an inner bore whose diameter, in an area facing the fastening head for the denture and remote from the spacer sleeve, is larger than the external diameter of the implant post, which holds the denture with a bearing surface engaging the ring shoulder. In one embodiment, the intermediate element is formed by a core element of a rigid material surrounded by a sleeve element of an elastic, plastic material.

23 Claims, 4 Drawing Sheets

ENOSSAL IMPLANT WITH AN ELASTIC INTERMEDIATE ELEMENT AND A METAL SPACER ELEMENT

BACKGROUND OF THE INVENTION

The present invention is directed to an enossal implant which is also known as an endosteal or endosseous implant. The implant has a base structure which is snugly mounted in a bone of the jaw and has a threaded internal bore for receiving a spacer element which threadably receives a metal implant post of a fastening head and fastening means. The spacer element is provided with a centering collar which is engageable with a shoulder on an upper edge of the base structure and receives an intermediate element made from an elastic, plastic material which will concentrically surround the implant post.

U.S. Pat. No. 4,793,808, whose disclosure is incorporated by reference and which corresponds to European Published Application 0216 931, discloses an implant in which a spacer sleeve has a bore open at both ends and is made of a plastic material. An intermediate element is directly inserted in the basic structure and in conjunction with the spacer sleeve assumes responsibility for the cushioning of the fastening head or denture with respect to the basic structure in all directions. In other words, it acts for cushioning the forces created by both vertical and lateral acting loads. Simultaneously, an electrical insulation is insured between the denture and the basic structure to prevent the occurrence of harmful creeping currents which can lead to corrosion and irritation of the body tissue.

The known implants in principle have proven satisfactory, but it has been found that the intermediate element, which not only has a bearing and dampening function but also a fastening function for the implant post, has a fatigue breakage tendency, particularly under tension. It has also been found that the extent of the dampening should possibly be adjustable so that greater flexibility is available to allow a greater variety of uses for the device.

SUMMARY OF THE INVENTION

The objects of the present invention are to provide an improved enossal implant or endosteal implant wherein the risk of fatigue breakage under tension is removed or at least drastically reduced and also the adjustability of the dampening function can be achieved to allow a higher positional precision for the denture.

According to the invention, these objects are obtained in that the spacer element is made from metal and is closed at its end remote from the fastening head for the denture and can be screwed into the basic structure. The intermediate element is inserted in a counterbore or socket in an opened end of the spacer element and is provided with a ring shoulder for engaging an upper edge of the spacer element. The intermediate element has an inner bore whose diameter in an area facing the fastening head for the denture and remote from the spacer element is larger than the external diameter of the implant post and that the implant post accompanied by the pressing of the bearing surface of the denture facing the intermediate element against the bearing shoulder of the intermediate element remote from the spacer element can be screwed into the spacer element.

The screwing-in depth of the implant post into the spacer sleeve can be made adjustable.

The invention also proposes that in an area in contact with the denture, the implant post has a plastic element or the like. According to another embodiment of the invention, the denture is elastically and/or easily displaceably mounted relative to the implant post in the axial direction thereof. A plastic ring or the like can be positioned between the denture and implant post. Alternately thereto, the elastic mounting of the denture with respect to the implant post is insured by a corresponding construction of the plastic envelope of the implant post head.

The invention also proposes that the counterbore or socket of the spacer element, which counterbore receives the intermediate element in a flush manner, is constructed so as to be tapered in cross section or to conically widen toward an open end thereof.

According to the invention, the implant post can be screwed with adjustable torque into the spacer element.

Another embodiment of the invention is characterized in that the basic structure and/or the exposed circumferential areas of the spacer element are both coated with a hydroxylapatite or the like.

According to the invention, the implant post can be coated with an adhesive at the lower end in the vicinity of the external threads of the post.

According to the invention, the intermediate element is made completely from an elastic material, such as plastic, while the inner bore of the intermediate element has a stepped width with the diameter of the region adjacent the spacer element essentially corresponding to the external diameter of the implant post and the other region of the bore, which is adjacent the fastening head of the denture, having a diameter larger than the external diameter of the implant post.

As described hereinbefore, the invention is based on the surprising finding that it is possible to solve the above-mentioned problem in a particularly appropriate and satisfactory manner by the intermediate elements being constructed as an inner sleeve according to the prior art, no longer serving as a supporting part for the implant post and as an electrically and mechanically insulating or dampening element and, instead of the cushioning or dampening effect being split-off from the fastening function. The metal implant post, in conjunction with the metal spacer element ensures a reliable and precise fixing of the denture in the basic structure. However, the dampening function is insured by the intermediate element concentrically surrounding the implant post with the dampening taking place in the vertical direction over the volume of the elasticity of the intermediate element which is variable with different torques used to fasten or tighten the implant post into the spacer element. The dampening function in the lateral direction is achieved by utilizing a vibrating bar principle for the implant post which is located in a correspondingly zonally widened inner bore of the intermediate element in conjunction with the material of the intermediate element. On pivoting the denture located on the implant post, compressive and tensile forces, as well as bending moments, are exerted on the intermediate element. The risk of fatigue breaks under the action of tension existing with the heretofore known implants is obviated by the present invention.

As in the prior art, polyoxymethylene can be used for the intermediate element. Optionally, through a corresponding choice of implant post material, it is possible to influence the rigidity of the system. Optionally, the lower end of the implant post in its screwed-in region, can be coated with an adhesive so that, in addition to the screwing-in action into the basic structure, there is an adhesive joint to prevent loosening. However, this joint can be easily released by applying sufficient torque in a direction for unscrewing the post from the spacer element. The supporting of the implant post and the intermediate element can actually take place at different levels and the rigidity can be influenced not only by this but also by the diameter changes of the implant post.

It has been found that in the case of the above-mentioned embodiment of the implant according to the invention, in which the intermediate element is made entirely from a plastic material and has a stepped width inner bore with a region of a diameter adjacent the spacer element substantially corresponding to the external diameter of the implant post and an upper region or area adjacent the denture fastening head being of a larger diameter than the external diameter of the implant post, the obtaining of a satisfactory vertical elasticity and, simultaneously, a satisfactory horizontal elasticity is still not completely insured in a satisfactory manner.

This is due to the fact that for obtaining an adequate vertical elasticity, the plastic materials from which the integral intermediate element is made must be relatively soft. Thus, the lateral elasticity can easily become too large because a pivoting movement of the implant post according to the vibrating bar principle is not offered a sufficiently large resistance by the intermediate element. In particular, the lateral deflection of the implant post operating according to the vibrating bar principle is not as reliably limited as would be desirable in the aforementioned embodiment of the implant according to the invention if, during the lateral deflection, the implant post engages on the wall of the inner bore of the intermediate element when the latter is made from a relatively soft plastic material.

In order to simply achieve both a satisfactory vertical elasticity and, simultaneously, a satisfactory lateral elasticity with a reliable lateral deflection of the implant post, the invention further proposes that the intermediate element be composed of a core element which is made of a relatively stiff material and is provided with a ring shoulder or engagement shoulder and that the element also includes an intermediate sleeve made from a relatively soft, elastic material surrounding the area of the ring shoulder or engagement shoulder. The intermediate core element can be made of rigid plastic, such as a polyoxymethylene or the like. According to the invention, the intermediate core can also be made from metal, such as, for example, titanium. According to the invention, the intermediate sleeve element is made from a flexible plastic, such as polyurethane or the like.

A further embodiment of the invention is characterized in that the intermediate core element has a sleeve-like construction and, in the vicinity of the ring shoulder and bearing shoulder, has a collar. The intermediate sleeve element can be positively connected to the intermediate core by utilizing such a collar. In one embodiment, the collar will have an undercut. The intermediate sleeve element can be shaped on the intermediate core by using an injection molding process.

According to the invention, the bore of the intermediate core element has a central area in the vicinity of the ring shoulder and the bearing shoulder in which the internal diameter of the bore substantially corresponds to the external diameter of the implant post. The smaller, internal diameter central region of the inner bore of the core element can have the same distance from the end faces of the core element. Alternatively thereto, it is also possible, according to the invention, for the smaller intermediate diameter central area of the inner bore of the core element to have a varying spacing from the end faces of the intermediate element.

Due to the fact that in the above-described embodiments the intermediate element is formed from two different components, namely an intermediate core element made from a rigid, hard material, preferably titanium, and an intermediate sleeve element, which at least zonally surrounds said hard core and is made from a soft, flexible plastic, it is possible, on the one hand, to reliably limit the lateral deflection of the implant post by the intermediate core element so that no excessive lateral deflections are possible. Simultaneously, a satisfactory vertical elasticity is insured because in the vicinity of the ring shoulder and the bearing shoulder there is a compressible, soft elastic plastic material, such as polyurethane for absorbing the vertical compressive stresses. In contrast to the prior art, which combined together the function of the fastening part for the implant post, on the one hand, the present invention has made the functions separate. In connection with the last-described embodiments, the invention proposes to further split-up the two cushioning or dampening functions of the intermediate element, namely the vertical elasticity, on the one hand, by constructing the intermediate element as a two-component construction with a hard core element and a soft sleeve element.

Also in the case of the last-described embodiment of the implant according to the present invention, the inner bore of the intermediate element can zonally undergo a diameter reduction in such a way that its internal diameter substantially corresponds to the external diameter of the implant post, although this is not absolutely necessary for the function of the intermediate element according to the invention. If the inner bore of the intermediate element or the intermediate core element has, over its total longitudinal extension, a larger diameter than the external diameter of the implant post, the implant post can be bent down to a limited extent within the inner bore of the intermediate core element and the transverse deflection, then, is limited when the implant post operates according to the vibrating bar principle strikes an upper edge of the inner bore. As stated, according to the invention, optionally, a central area of the inner bore corresponds to the external diameter of the implant post. If the center area is located symmetrically in the longitudinal center, the intermediate element is built up in a completely symmetrical manner and can be mounted in either direction. However, in a case where the central area is asymmetrical with respect to the longitudinal center of the intermediate element, a function of the intermediate element mounting direction will provide different lateral elasticity and dampening characteristics of the intermediate element.

Other advantages and features of the invention will be readily apparent from the following description of the preferred embodiments, the drawings and claims.

DESCRIPTION OF THE PREFERRED EMBODIMENTS

Figure 1:
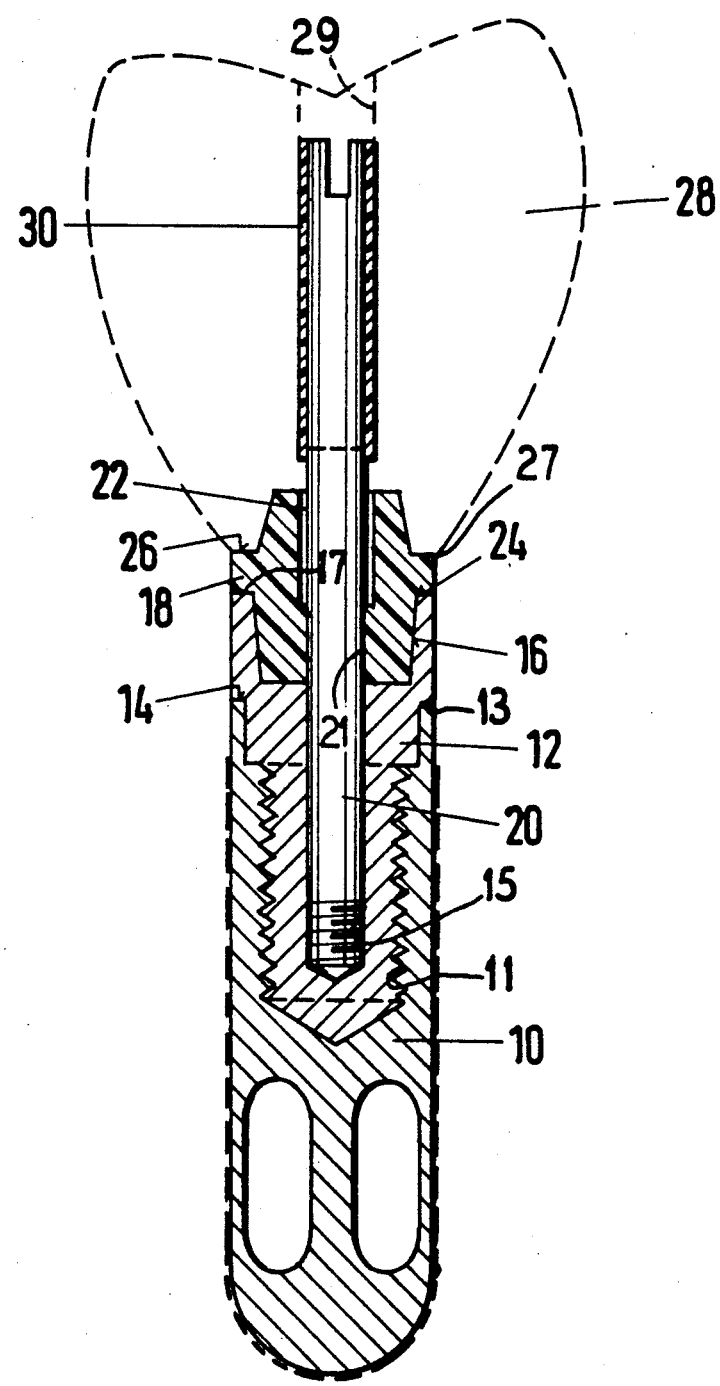
FIG. 1 is a longitudinal cross sectional view with portions in elevation of an endosteal implant according to the present invention.

The principles of the present invention are particularly useful when incorporated in an endosteal implant of FIG. 1. The implant of FIG. 1 includes a basic structure or member 10 which is preferably made of titanium and is coated on its outer face, which will come in contact with the body tissue, with a hydroxylapatite. As mentioned above, the function of the basic structure is its implantation in the bone of the jaw. The basic structure is provided with a threaded bore 11 which has an annular upper surface or shoulder 14. A spacer element 12, which is formed of titanium and has external threads, is screwed or threaded into the threaded bore 11 of the structure 10. The spacer element 12 has a shoulder 13 which engages the surface or shoulder 14 on the upper edge of the basic structure 10 in a manner apparent from the drawings. The element 12 is closed at its lower end facing the basic structure and has an inner bore 15, which is provided with internal threads. The bore 15 has a counterbore forming a widening or socket 16 on the upper end of the element 12. This widening or socket forms a centering collar. A circumferential surface of the spacer element 12, which comes into contact with the body tissue, is coated with the body tissue-friendly hydroxylapatite in a manner similar to the basic structure 10.

An elastic intermediate element 18, which is made from polyoxymethylene is inserted in the socket or widening 16 of the spacer element 12 and has an axial bore with a lower bore region 21 adjacent the spacer element with an internal diameter substantially corresponding to an external diameter of a titanium implant post 20. However, an upper bore region 22 has a much larger diameter than the external diameter of the post 20. The post 20 is also provided on its lower end with threads for being threaded into the corresponding internal threaded bore 15 of the element 12. The intermediate element 18 has a ring shoulder 24 which engages an upper edge or shoulder 17 of the spacer element 12. The ring shoulder 24, on an upper surface, has a bearing shoulder 26 which engages a lower bearing face 27 of a denture 28. The implant post 20 is provided on its upper end with a plastic envelope 30 which engages the internal surface of a bore 29 of the denture 28 and holds the denture with its shoulder 27 on the shoulder 26 of the elastic intermediate element 18.

It is important in the above-described construction that the implant post 20 freely traverses the upper region 22 of the inner bore of the elastic intermediate element 18 without engaging on the inner wall of the inner bore of this element. As a function of the screwing-in depth of the implant post 20 or as a function of the heightwise construction considered in the axial direction of the implant post 20 of the upper region 22 of the elastic intermediate element 18, the height area in which the implant post freely traverses the intermediate element is adjustable. As a function of the height of the upper area 22 of the intermediate element 18 in which the implant post 20 does not engage on the inner wall of the bore of the intermediate element, the rigidity of the "vibrating rod" formed by the implant post 20 is higher or lower. With respect to the implant post 20, the denture 28 is mounted in an easily displaceable or vertically resilient manner. It is possible to modify the length of the implant post 20 to adapt the particular "installation height". This is either brought about by interposing a corresponding plastic ring or a corresponding construction of the plastic envelope 30. The plastic envelope 30 always prevents an electrically conductive contact between the denture 28 and the implant post 20 so that it insures that the denture 28 is electrically insulated from the basic structure 10. This prevents harmful creeping currents, which can lead to corrosion and the like. In addition, the denture 28 is elastically resilient mounted in all directions with respect to the basic structure 10. This is, first, assured by the "vibrating rod" action of the implant post 20 and also by the elastic dampening action against vertical forces in the axial direction of the implant post 20 caused by the intermediate element 18. The elasticity or cushioning insured by the intermediate element 18 can also be varied by tightening the implant post 20 with different torques.

Figure 2:
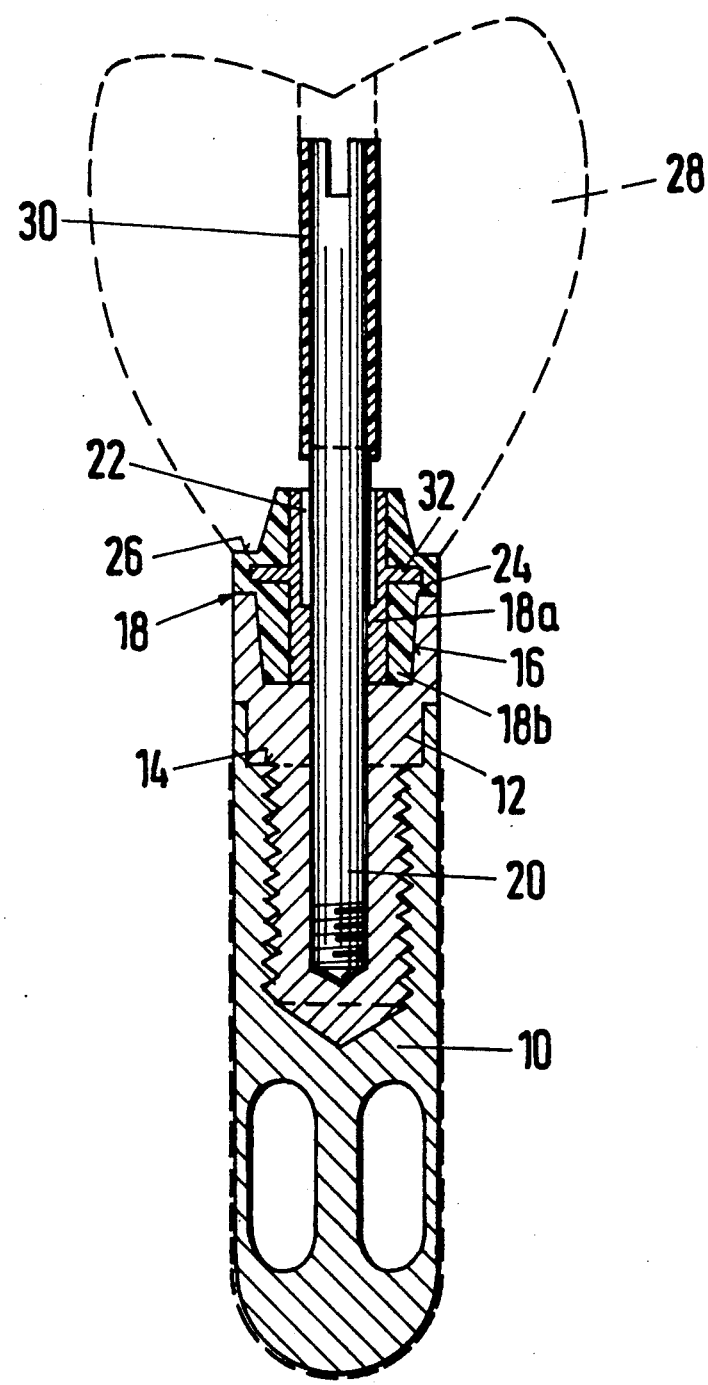
FIG. 2 is a longitudinal cross sectional view with portions in elevation of an embodiment of the endosteal implant according to the present invention.

In the embodiment of FIG. 2, the structure of the basic structure 10 and the titanium spacer sleeve 12 are substantially the same. The spacer element 12 has the widening 16, which, as illustrated in both embodiments, has a slight outward conical tapering so that the mouth of the widening is of a greater diameter than the base.

In the embodiment of FIG. 2, the intermediate element 18, which is inserted in the socket 16 of the spacer element 12, is made from a rigid, hard intermediate core element 18a, preferably of titanium, and a relatively flexible elastic intermediate sleeve element 18b, which is preferably made of polyurethane. In the lower region facing the spacer element 12, the inner bore of the core element 18a has an internal diameter which substantially corresponds to the external diameter of the titanium implant post 20. However, in an upper bore region 22, the diameter is greater than the external diameter of the post 20. On its lower end facing the basic structure 10, the implant post 20 has external threads by means of which it can be screwed into the threaded bore of the spacer element 12. The intermediate element 18 engages with a ring shoulder 24 on the upper edge of the spacer element 12. The lower bearing face of the denture 28 engages a bearing shoulder 26 of the ring shoulder 24 of the intermediate element and, at its upper end, the implant post is provided with a plastic envelope 30, which resiliently mounts the denture on the post.

With regard to the operation of the above-described construction, the advantages are the same except that the intermediate element 18 has the core element 18a and the sleeve element 18b. The core element 18a, as illustrated, has a collar 32 which serves to help keep the sleeve element 18b in place on the core element. The sleeve element 18b can be provided on the core element 18a by an injection molding process.

Figure 3:
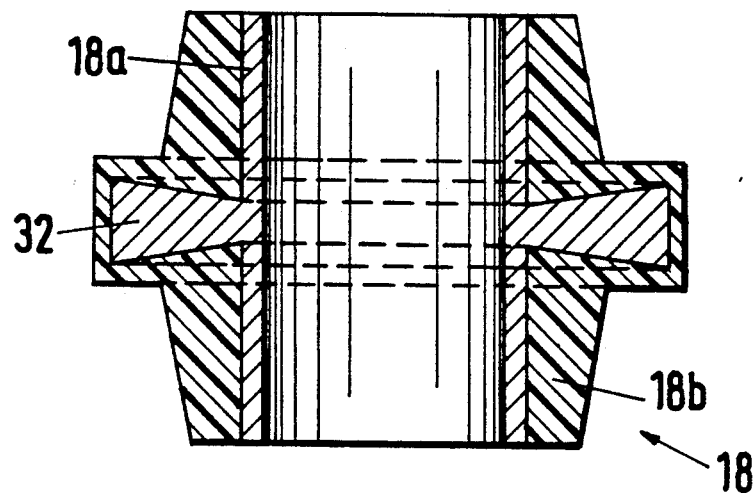
FIG. 3 is an enlarged cross sectional view of a modification of the intermediate element of FIG. 2.
Figure 4:
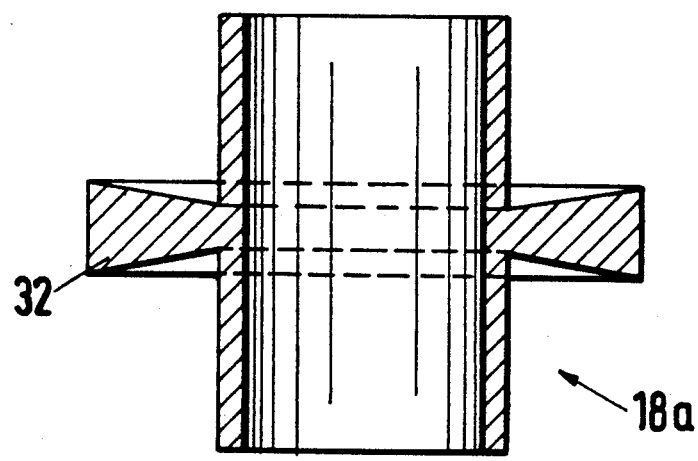
FIG. 4 is an enlarged cross sectional view of the core element of the intermediate element of FIG. 3.

A modification of the intermediate element 18 of FIG. 2 is shown in FIG. 3. In this modification, the core element 18a is formed of titanium and has a collar 32 which is constructed to have undercuts. The sleeve element 18b is applied by injection molding and the undercuts help facilitate a firm engagement between the core element 18a and the sleeve element 18b.

In the modification of FIG. 3, the internal diameter of the bore of the core element 18a is constant and is preferably slightly greater than the diameter of the rod being received therein.

Figure 5:
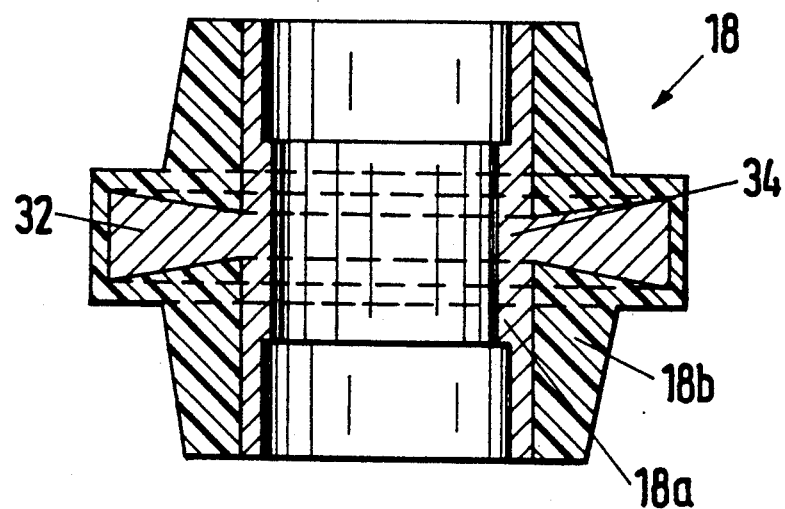
FIG. 5 is an enlarged cross sectional view of another modification of the intermediate element of FIG. 2.
Figure 6:
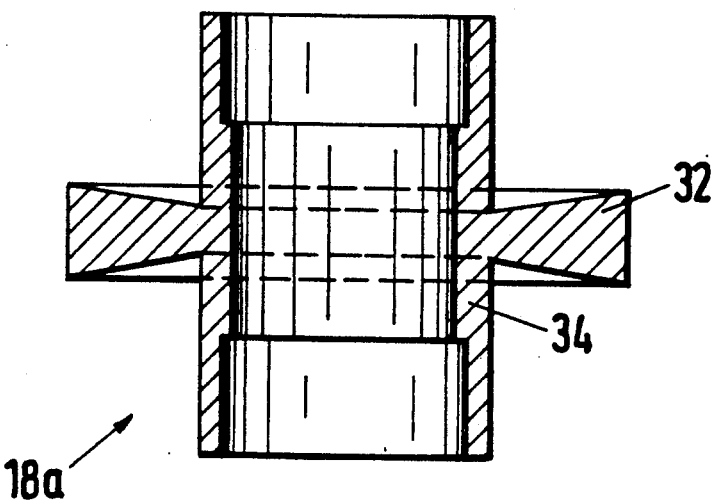
FIG. 6 is an enlarged longitudinal cross sectional view of the core element of the modification of FIG. 5.

Another modification of the intermediate element is illustrated in FIGS. 5 and 6 and, in this modification, the core element 18a has, in its central region 34, along the direction of the medium longitudinal axis, a smaller internal diameter which corresponds to the external diameter of the implant post 20, such as illustrated in FIG. 2. The central region 34 is equal distance from the upper and lower end faces, as shown in the drawings, so that the intermediate element 18 can be installed in the implant in either direction without changing the horizontal or transverse elasticity characteristics. Naturally, an embodiment is also possible in which the central region 34 is arranged asymmetrical with respect to the medium longitudinal axis of the intermediate element 18 and then different horizontal or transverse elasticity characteristics would be obtained as a function of the mounting direction of the element 18.

As a result of the inventive construction of the intermediate element 18, namely sub-dividing it into two components, a hard intermediate element core 18a and a flexible elastic intermediate sleeve element 18b are provided. It is, thus, insured that the case of vertical stressing in the vicinity of the ring shoulder 24 and the bearing shoulders 26 relatively flexible elastic plastic material is available which will insure a satisfactory vertical deformation. Simultaneously, the hard material of the intermediate core element 18a prevents an undesirable pronounced lateral deflection in the case of the transverse stressing by bending of the implant post 20.

Although various minor modifications may be suggested by those versed in the art, it should be understood that we wish to embody within the scope of the patent granted hereon all such modifications as reasonably and properly come within the scope of our contribution to the art.

We claim:

1. An enossal implant comprising a basic structure for snugly receiving in a bore in a jaw of a patient, said basic structure having a threaded bore surrounded by an annular shoulder at an upper end, a spacing element being composed of metal and having external threads for securing the spacing element in the threaded bore of the basic structure with a first annular shoulder of the spacing element engaging the annular shoulder of said basic element, said spacing element having an axial bore with a threaded portion and a counterbore adjacent the end opposite a closed end of the spacing element forming a second annular shoulder, an intermediate element being inserted in said counterbore and having a ring shoulder engaging said second annular shoulder of the spacing element, the intermediate element having an inner bore aligned with the axial bore of the spacing element, and an implant post having a threaded portion and extending through the intermediate element to be threaded into the threaded portion of the axial bore of the spacing element, said intermediate element having at least a portion of the bore of a diameter greater than an external diameter of said implant post, said ring shoulder of the intermediate element being of a plastic material having an annular surface engageable by a bearing face of a denture secured by said post on said base structure.

2. An implant according to claim 1, wherein the amount of threading-in of the implant post into the spacer element is adjustable.

3. An implant according to claim 1, wherein the implant post has a plastic envelope in the area coming in contact with said denture.

4. An implant post according to claim 1, wherein the denture is mounted elastically on the implant post.

5. An implant according to claim 4, wherein the elastic mounting of the denture on said post includes a plastic ring interposed therebetween.

6. An implant according to claim 1, wherein the denture is elastically mounted on the implant post by a plastic envelope at a head of said implant post.

7. An implant according to claim 1, wherein the counterbore of the spacer element receiving the intermediate element in a flush manner has a conical expansion to form a frusto conical cross section.

8. An implant according to claim 1, wherein the implant post can be threaded into the spacer element with an adjustable torque.

9. An implant according to claim 1, wherein all exposed surfaces of the basic structure and the spacer element are coated with a hydroxylapatite.

10. An implant according to claim 1, wherein the implant post can be coated with an adhesive at the lower end of the vicinity of its external threads.

11. An implant according to claim 1, wherein the intermediate element is completely made of an elastic material, said elastic material being a plastic, and the inner bore of the intermediate element has a portion of a diameter corresponding to the external diameter of the implant post being provided adjacent the spacer element so that the portion of the bore having the larger external diameter is adjacent the denture.

12. An implant according to claim 1, wherein the intermediate element is composed of a core element for surrounding the implant post made of a relatively rigid material, and a sleeve element made of a relatively soft elastic material surrounding the core element in the area of the ring shoulder.

13. An implant according to claim 12, wherein the core element is made from a rigid plastic selected from polyoxymethylene.

14. An implant according to claim 12, wherein the intermediate core is made of a metal.

15. An implant according to claim 14, wherein the core element is made from titanium.

16. An implant according to claim 12, wherein the sleeve element is made of a flexible plastic polyurethane.

17. An implant according to claim 12, wherein the core element has a sleeve-like construction and a collar is provided in the vicinity of the ring shoulder and bearing shoulder.

18. An implant according to claim 17, wherein the sleeve element is positively connected to the intermediate core element.

19. An implant according to claim 17, wherein the collar has an undercut.

20. An implant according to claim 17, wherein the sleeve element is shaped by injection molding process on the core element.

21. An implant according to claim 12, wherein the core element has an inner bore with a central region in the vicinity of the ring shoulder having an internal diameter corresponding to the external diameter of the implant post.

22. An implant according to claim 21, wherein the central region of the small internal diameter is equal distance from the end faces of the intermediate element.

23. An implant according to claim 21, wherein the central region of a smaller internal diameter has a varying spacing from the end faces of the intermediate element.

* * * * *